(12) United States Patent
Schames

(10) Patent No.: US 6,581,603 B1
(45) Date of Patent: Jun. 24, 2003

(54) ORAL APPLIANCE

(76) Inventor: Joseph Schames, 110 S. Poinsettia Pl., Los Angeles, CA (US) 90036

( * ) Notice: Subject to any disclaimer, the term of this patent is extended or adjusted under 35 U.S.C. 154(b) by 0 days.

(21) Appl. No.: 10/016,884

(22) Filed: Dec. 14, 2001

(51) Int. Cl.[7] ................................................. A61F 5/56
(52) U.S. Cl. ....................... 128/848; 128/859; 128/861; 128/862
(58) Field of Search ............................... 128/846, 848, 128/859–862; 433/6, 215

(56) References Cited

U.S. PATENT DOCUMENTS 5,277,203 A * 1/1994 Hays ........................... 128/861
5,730,599 A * 3/1998 Pak ............................. 433/215
5,795,150 A * 8/1998 Boyd ............................. 433/6
5,816,802 A * 10/1998 Montgomery ............... 128/861

* cited by examiner

Primary Examiner—Michael A. Brown
(74) Attorney, Agent, or Firm—Allan M. Shapiro

(57) ABSTRACT

The oral appliance engages over the mandibular incisors and presents a flat raised upper contact surface which is sufficiently wide to contact at least part of one of the two upper center incisors and preferably both of them. This prevents tooth contact between the upper and lower dental arches to prevent grinding of the teeth. It prevents contact of the upper canine teeth with any teeth or the appliance so as to decrease the facial muscular tension which is sometimes associated with headaches and migraines. Application of the appliance to the lower dental arch is phonetically and aesthetically superior to other configurations and arrangements.

22 Claims, 3 Drawing Sheets

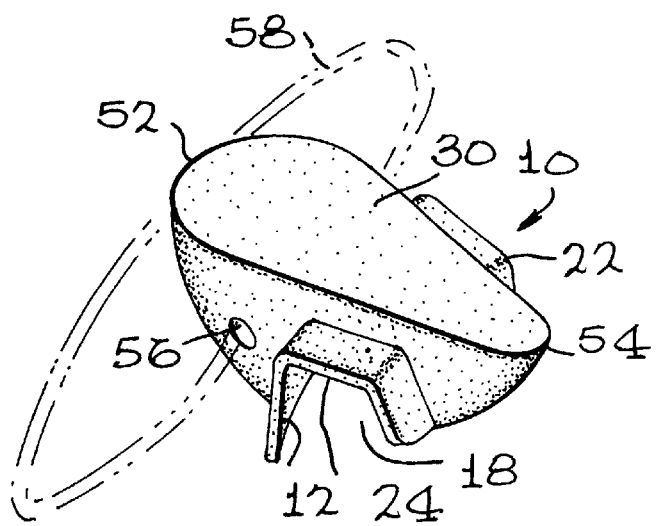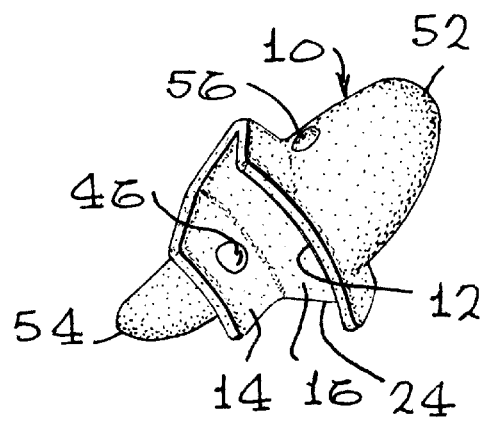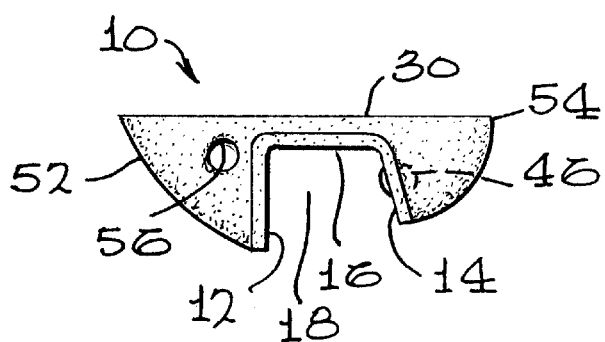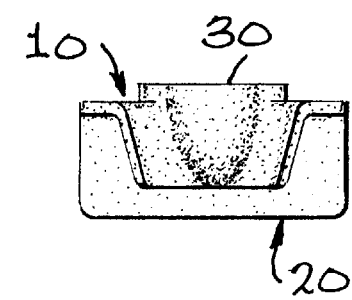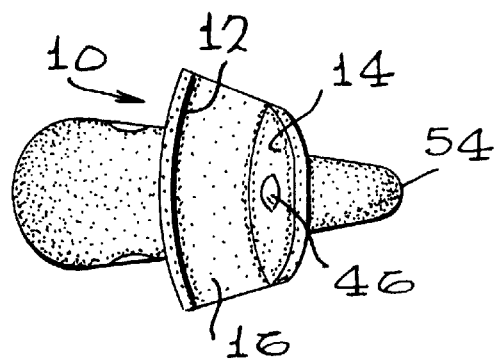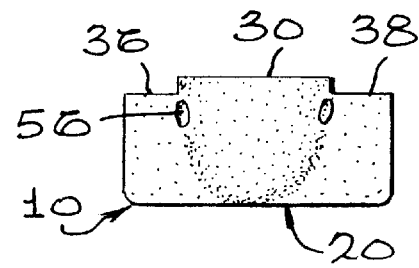

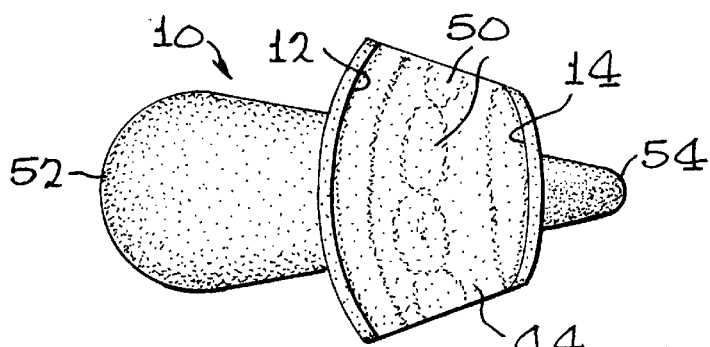
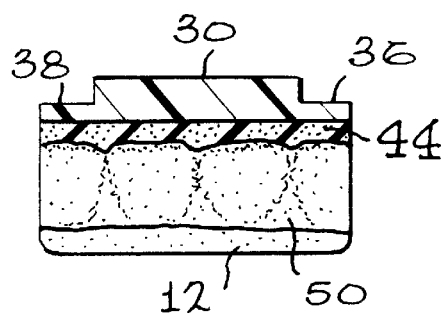
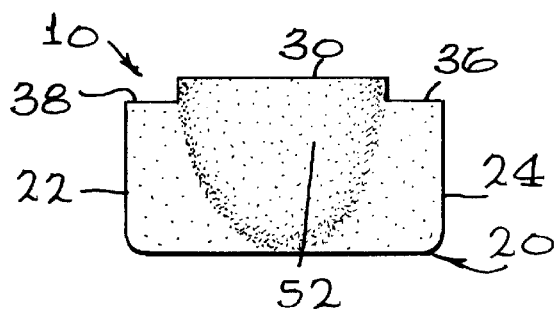
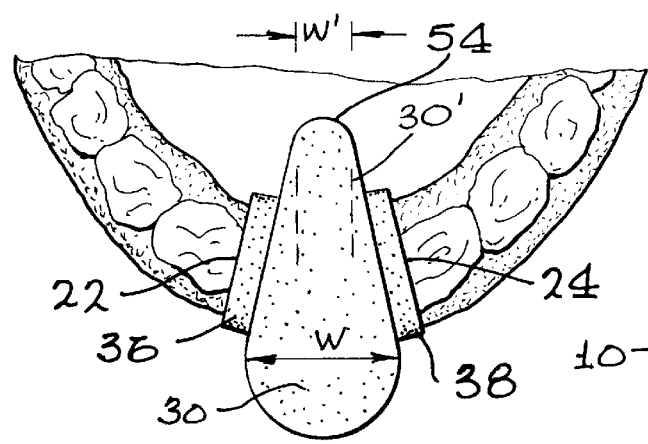
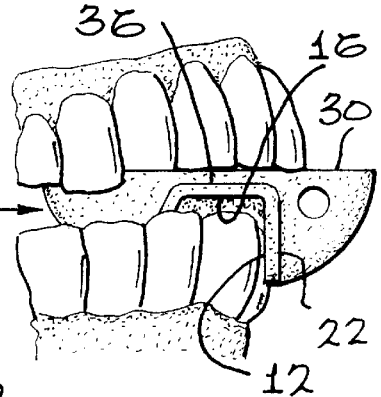
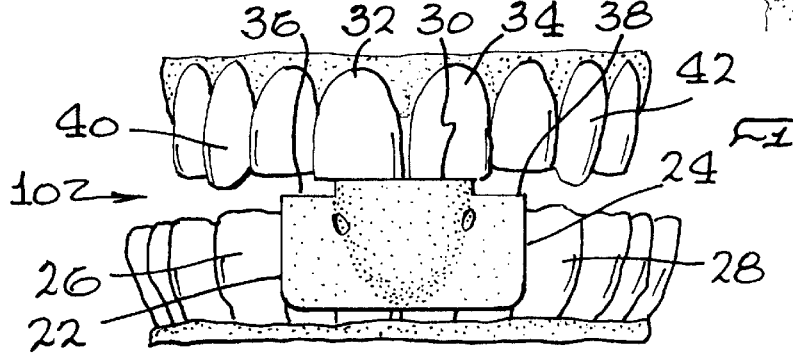

ORAL APPLIANCE

FIELD OF THE INVENTION

This oral appliance is a body, having a curved trough sized to fit over the lower anterior teeth, to protect the user's teeth in the event of the user's clenching and/or grinding of his teeth and to reduce facial muscle tension and tooth wear.

BACKGROUND OF THE INVENTION

Grinding and clenching of the teeth have been shown to increase under stress and by anticipation of stressful events. The increased pressure and lateral movement against tooth surfaces produce fractures and/or wearing down of teeth surfaces.

Grinding and clenching also cause increased tension and contraction of facial musculature. This can cause facial pain and can contribute to muscle tension headaches and migraines. Increased muscle tension and contraction cause fatigue, spasming and cramping of the facial muscles resulting in pain and limitation of motion of the mandible. Patients suffering from these symptoms are typically treated with a mouth appliance such as described by Norton in U.S. Pat. No. 4,671,766 and Sullivan in U.S. Pat. No. 4,519,386.

The appliances generally used are custom made by the dentist for covering the user's full upper or lower arches. Unfortunately, in most cases, full arch appliances still allow the grinding and clenching to exist on the appliance, without long lasting marked reduction in facial muscular tension and contractions. Other appliances as described by Hays in U.S. Pat. No. 5,277,203 and by Boyd, Sr., in U.S. Pat. No. 5,513,656 are used on the upper teeth. These upper appliances can allow for the opposing mandibular canine teeth to come in contact with the appliance. The contact of the opposing canine teeth with the appliance initiates increased facial muscular tension.

Most appliances are custom fabricated and fitted by a In dentist for the individual, usually at a prohibitive cost of hundreds to thousands of dollars. Other appliances can be ingested, inhaled or lost, thereby causing danger and cost to the user.

Therefore, there is a continuing need for simplifying and improving means and methods for the prevention of damage to teeth and in the reduction of facial muscular tension and contraction as it relates to facial pain, headaches, migraines and temporomandibular disorders.

SUMMARY OF THE INVENTION

In order to aid in the understanding of this invention, it can be stated in essentially summary form that it is directed to an oral appliance which is comprised of a body having a curved trough on the under side thereof for the placement therein of thermoplastic material for fitting onto the lower anterior teeth, i.e., the mandibular incisors. The body includes a flattened raised ramp extending anteriorly and posteriorly on the top of the appliance when the appliance is set over the lower incisors to prevent contact between the upper and lower posterior teeth and to prevent the opposing upper canine teeth from coming into contact with the lower teeth or with the appliance. The ramp is sufficiently wide to contact at least part of one of the two upper center incisors and preferably both of them.

It is thus a purpose and advantage of this invention to provide the user with a self-fitting, customized appliance for placement on the lower incisors without the need of seeing a dentist for fabrication, fitting and adjustments of the appliance. The placement of the oral appliance on the lower incisors is very much superior to placement on the upper arch. A phonetic advantage is achieved because placement of an appliance on the upper arch interferes with the tongue position during speaking while placement on the mandible incisors permits the user to speak more clearly. Similarly, the placement of the oral appliance on the mandible is aesthetically superior because it is less visible, being largely hidden behind the upper incisors and the lips.

It is another purpose and advantage of this invention to provide a prefabricated curved trough to correspond to the general curvature of the lower central and/or lateral incisors which is retained by a thermoplastic material within the trough. After heating and molding of the thermoplastic material, the appliance is placed over the lower incisor teeth.

It is a further purpose and advantage of this invention to provide a self-fitting customized appliance which has a flat, raised ramp parallel to the horizontal line of the bite which in allows the upper central incisor teeth to rest on this ramp, discluding the remaining posterior and canine teeth even when the mandible is moved in all excursions.

It is a further purpose and advantage of this invention to provide an oral appliance which has a hollow channel for a necklace line to be inserted to help prevent ingestion, inhalation and/or loss of the appliance.

It is a further purpose and advantage of this invention to provide an oral appliance which has a reservoir in its posterior extension which allows for a radio-opaque material to be placed within. This provides a radiographic means of location if ingested or inhaled.

The features of this invention which are believed to be novel are set forth with particularity in the appended claims. The present invention, both as to its organization and manner of operation, together with further objects and advantages thereof, may be best understood by reference to the following description, taken in conjunction with the accompanying drawings.

BRIEF DESCRIPTION OF THE DRAWINGS

FIG. 1 is a perspective view of the oral appliance of this invention as seen from an upper posterior position.

FIG. 2 is a perspective view of the oral appliance of this invention from a lower anterior view.

FIG. 3 is a side elevational view thereof.

FIG. 4 is a view from the posterior side.

FIG. 5 is a bottom view.

FIG. 6 is an elevational view from the anterior.

FIG. 12 is a bottom view of the appliance of FIG. 11, enlarged with respect to FIG. 5 and showing the dental impression of the lower incisors therein.

FIG. 13 is a section similar to FIG. 8, but showing the dental impression of the lower incisors in the thermoplastic material in the oral appliance.

FIG. 14 is a view of the anterior end thereof.

FIG. 15 is a plan view of the oral appliance as shown installed on the center mandibular incisors.

FIG. 16 is an anterior view thereof.

FIG. 17 is a lateral view thereof, showing engagement of the oral appliance on the mandibular incisors and the upper incisors in contact with the top surface ramp of the oral appliance.

DESCRIPTION OF THE PREFERRED EMBODIMENTS

Figure 7:
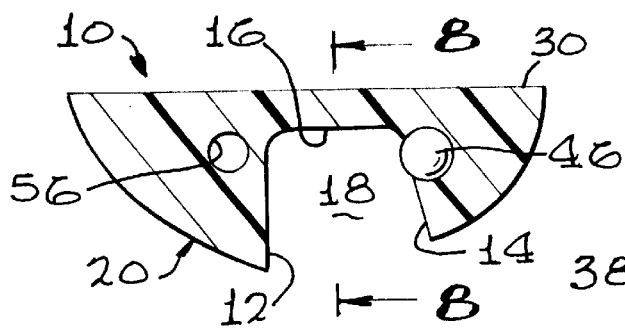
FIG. 7 is a central section through the appliance, enlarged as compared to FIG. 3.
Figure 8:
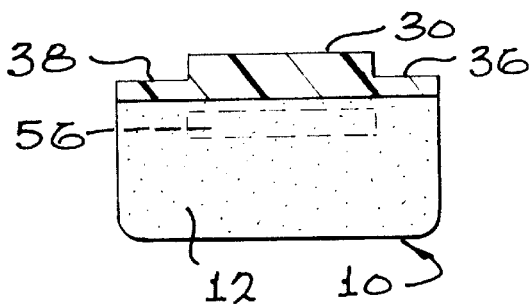
FIG. 8 is a section taken generally along line 8—8 of FIG. 7.

The oral appliance of this invention is generally indicated at 10 in FIGS. 1–17. The oral appliance 10 protects the user's teeth from being fractured and from being worn down, because of clenching and grinding of the teeth. The oral appliance 10 also acts to decrease the facial muscular tension which can be partial causation for headaches and migraines. The oral appliance 10 is configured to prevent full closure of the mandible, thereby reducing pressure within the temporomandibular joints. The oral appliance 10 comprises anterior and posterior surfaces 12 and 14 which, together with top surface 16, form a trough which is numerically identified at 18 in FIGS. 1, 3 and 7. The trough 18 is formed in the body 20 of the oral appliance. The trough has a length which, when viewed posteriorly, is formed by the right end 22 and left end 24 of the body. As seen in FIG. 16, the length between the left and right ends is sufficient to substantially cover the four lower incisors, and not reach the lower canines 26 and 28. The trough 18 is curved, especially the anterior surface 12, see FIG. 5, to accommodate for the forward arch of the lower incisors, see FIG. 12. The body can be made of synthetic polymer composition material.

The body 20 also carries an upper incisor contact surface 30 which is a flat ramp. The ramp lies generally in the tooth plane. The width of the anterior end of the ramp, "W" in FIG. 15, is illustrated as being substantially as wide as the two center upper incisors 32 and 34, see FIG. 16. However, the width W may be narrower so that only one of the upper incisors, and even only a part of one of the upper incisors, contacts the ramp 30. The narrower ramp 30' is indicated in broken lines and as having a width W'. The narrower contact may be particularly useful when the location, shape and/or size of the upper incisors are not uniform or symmetrical. However, contact with the two central upper incisors is preferred for optimally minimized stress concentration.

The body 20 is cut down to lower surfaces 36 and 38 beside the ramp 30, see FIGS. 6, 8, 13, 14, 15, 16 and 17, so that the upper canines 40 and 42 do not come into contact with the ramp 30 or other parts of the appliance 10, upon lateral mandibular motion. Placement of the oral appliance 10 on the lower incisors prevents the upper canines from coming into contact with the appliance or other teeth. This freedom of the canines from contact tends to reduce facial muscular tension. Furthermore, as seen in FIG. 3, the height of the oral appliance, that is, the distance from the top 16 of the trough 18 to the upper contact surface 30, is small compared to previous practice so that this decrease in opening between the upper and lower teeth does not initiate the increase of muscular tension associated with other appliances. The placement of the oral appliance on the lower incisors is very much superior to placement on the upper arch. A phonetic advantage is achieved because placement on the lower mandible creates less interference with tongue position during speaking so that the user can speak more clearly. Similarly, the placement of the oral appliance on the mandible is aesthetically superior because of its reduced visibility.

Figure 9:
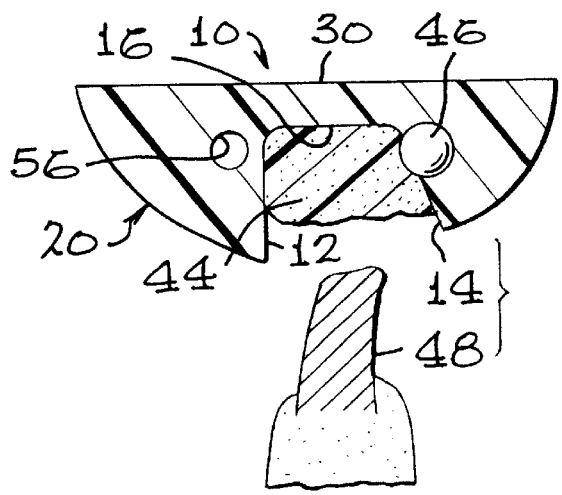
FIG. 9 is a view similar to FIG. 7, showing thermoplastic material installed in the appliance and the lower anterior teeth about to make an impression therein.
Figure 11:
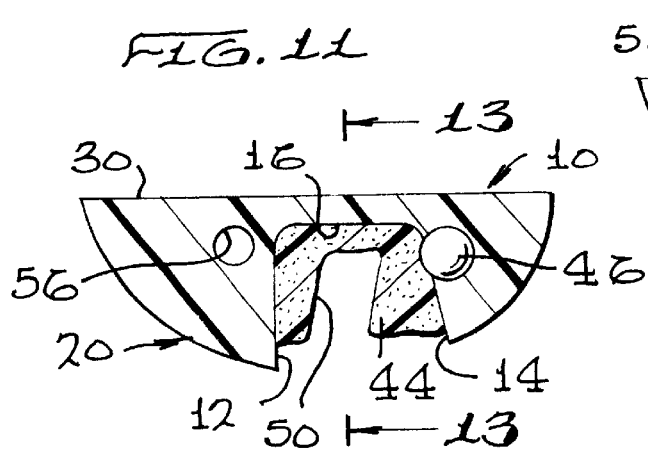
FIG. 11 is a view of the appliance similar to FIGS. 9 and 10, after the appliance is removed from the anterior teeth.
Figure 10:
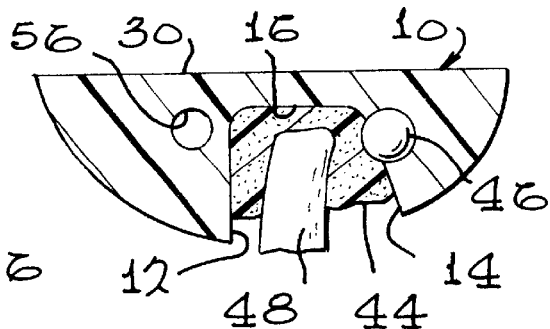
FIG. 10 is a view similar to FIG. 9, showing the lower anterior teeth making the impression.

The oral appliance 10 is personally fitted to the user by the installation of a thermoplastic material 44 in the trough 18, see FIGS. 9, 10, 11 and 12. Before installation of the thermoplastic material, a radio-opaque member 46 is installed in the corresponding recess in the wall 14 which defines the posterior surface, see FIGS. 7, 9, 10 and 11. The thermoplastic material 44 keeps the radio-opaque member 46 in place. The radio-opaque member can be a small steel ball, or the like. After the thermoplastic material 44 is installed, as seen in FIG. 9, the dental impression is made therein by means of the lower incisors 48, see FIG. 10. When the thermoplastic material is sufficiently hardened, the oral appliance with the molded thermoplastic material is removed from the teeth to leave a tooth impression 50, see FIGS. 11, 12 and 13. The oral appliance thus is fitted over the user's lower anterior incisors and is held in place by means of the personalized fit between the incisors and the tooth impression material. As also is apparent from FIGS. 10, 11 and 17, the lower incisors extend only part way into the dental material so that they do not contact the bottom 16 of the trough 18 (see FIG. 7), thus assuring that the lower incisors do not contact the body 20 of the appliance. Once in place, the flat ramp surface 30, which extends both anteriorly and posteriorly of the tooth arch, comes in contact with one or both of the center two upper incisors. This prevents the upper and lower back teeth from contacting the opposing back teeth when the mouth is closed. The oral appliance 10 prevents the upper canine teeth 40 and 42 from contacting any other teeth.

In addition, due to the width of the ramp 30 at the dental arch line being narrower then the body 20, the appliance 10 prevents the upper canines 40 and 42 from contacting the appliance 10 even when the mandible moves from side to side. The appliance not only protects the teeth from contacting and damaging each other, but also reduces the tension and contraction of the facial muscles used in mastication. The flat ramp also allows the user to perform mandibular exercises, using the ramp as a guide. The ramp allows the mandible to be moved forward and backward and side to side without any inter-dentular interference.

The upper contact surface 30 extends both anteriorly and posteriorly with respect to the trough 18 so as to permit forward and backward mandibular motion. The anterior portion 52 and posterior portion 54 of the body 20, as best seen in FIG. 3, respectively extend forwardly and rearwardly of the walls which define the trough 18, to permit this motion. The anterior portion contains a hole 56 therethrough, through which can be positioned a necklace 58, see FIG. 1. The necklace can retain the oral appliance in convenient position when not in use, and can prevent swallowing of the oral appliance when it is in use. The radios-opaque member 46 permits determination of the location of the oral appliance by X-ray, should it be ingested or inhaled. The oral appliance 10 is to be removed by the user when eating or drinking. The appliance is to be used while sleeping. It is to be used during stressful and/or painful occasions during the day. It is also to be used throughout the day as a guide for therapeutic motion exercises that can be performed using the horizontal flat ramp 30 as a guide for these exercise movements of the mandible as the mandible moves anteriorly and posteriorly and side-to-side.

This invention has been described in its presently contemplated best modes and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. An oral appliance for humans comprising:
   a body, walls in said body defining a trough sized to receive thermoplastic material which can be molded to a shape to receive only lower incisors partially into said material;
   a flat upper contact surface on said body, said upper contact surface being sized to be engaged by at least part of one of the upper incisors but being sized to be away from the upper canines, even with substantial lateral mandibular motion.

2. The oral appliance of claim 1 wherein said upper contact surface extends anteriorly and posteriorly over only incisors on the lower dental arch, when positioned thereon, said upper contact surface being sufficiently far from said trough to prevent contact between the upper and lower posterior teeth.

3. The oral appliance of claim 2 further including thermoplastic molding material in said trough.

4. The oral appliance of claim 1 wherein said body is sufficiently thick between said trough and said upper contact surface and said upper contact surface is sufficiently narrow in the lateral direction so that, when said oral appliance is positioned on only lower incisors, there is no contact between the upper canine teeth with any of the lower teeth or with said oral appliance.

5. The oral appliance of claim 3 wherein said filling material is a thermoplastic material which has a softening and molding temperature of about 150° F.

6. The oral appliance of claim 1 wherein said body is made of synthetic polymer composition material.

7. The oral appliance of claim 6 wherein the anterior portion of said body has attachment structure thereon for attachment of a necklace thereto.

8. The oral appliance of claim 6 wherein said body has a recess therein and there is radio-opaque material in said recess.

9. The oral appliance of claim 1 wherein said upper contact surface is sized to be engaged by one of the upper incisors.

10. The oral appliance of claim 4 wherein said upper contact surface is sized to be engaged by one of the upper incisors.

11. The oral appliance of claim 1 wherein said upper contact surface is sized to be engaged by only the two center upper incisors.

12. The oral appliance of claim 4 wherein said upper contact surface is sized to be engaged by only the two center upper incisors.

13. An oral appliance for humans comprising:
    a body, a flat upper contact surface on said body;
    a trough in said body opposite said contact surface, said trough being defined by an anterior surface, a posterior surface and a top surface, said trough being sized to engage over the lower incisors between said surfaces, said top surface being spaced from said upper contact surface a distance sufficient to prevent the user's lower dental arch from contacting his upper dental arch when said oral appliance is in position over the user's lower incisors and with the user's upper incisors being in contact with said upper contact surface, said body being sufficiently narrow at said upper contact surface in the lateral direction along the dental arch so that normally only one, two or a part of one of the two center upper incisors engage said upper contact surface and so that, even when there is substantial lateral mandibular motion, the user's upper canine teeth do not contact said oral appliance or any lower teeth.

14. The oral appliance of claim 13 wherein said trough is wider than at said upper contact surface so that said trough can engage a greater distance along the lower incisors than the upper incisors engage on said upper contact surface.

15. The oral appliance of claim 14 further including a dental molding material in said trough, said dental molding material being moldable to form recesses which receive the lower incisors part way into said trough.

16. The oral appliance of claim 15 wherein there is dental molding material within said trough and there is a lower incisor tooth impression in said molding material.

17. The oral appliance of claim 16 wherein there is a recess in said body open to said trough and there is a radio-opaque member in said recess, said dental molding material retaining said radio-opaque member in said recess.

18. The oral appliance of claim 15 wherein the anterior end of said body extends from the user's mouth when positioned on his lower incisors and there is attachment structure on said anterior end for the attachment of a necklace thereto to retain control of said oral appliance when it is away from the user's lower incisors.

19. The oral appliance of claim 18 wherein said attachment structure is an opening through the anterior portion of said body and there is a necklace engaged through said opening so that the necklace can be employed to hold said oral appliance when said oral appliance is away from the user's lower incisors.

20. The method of protecting the user's teeth from being worn down or otherwise damaged due to clenching of the mouth and/or grinding of the teeth comprising the steps of:
    forming an oral appliance with a body having a laterally directed trough in the lower portion thereof and an upper contact surface on the top thereof;
    placing dental molding material in said trough;
    placing the oral appliance in the user's mouth and engaging it over the user's lower incisors so that the lower incisor impression is formed in the molding material to releaseably retain the oral appliance on the lower incisors;
    releaseably positioning the oral appliance in the user's mouth on his lower incisors with the upper contact surface being sized and.positioned so that, when his upper incisors are engaged on the contact surface, there is no interengagement between the teeth of the upper dental arch with the teeth of the lower dental arch and there is no contact between the upper canines and the oral appliance.

21. The method of claim 20 further including the step of:
    attaching a necklace to the oral appliance to retain control of the oral appliance when it is not engaged on the user's lower incisors.

22. The method of claim 20 further including the step of:
    positioning a radio-opaque member within the body of the oral appliance so that, if the user accidentally swallows the oral appliance, the position of the oral appliance inside the user can be identified by X-ray.

* * * * *